(12) United States Patent
Djordjevic et al.

(10) Patent No.: US 7,900,362 B2
(45) Date of Patent: Mar. 8, 2011

(54) MINIATURE DISPOSABLE SAFETY SCALPEL

(75) Inventors: Ilija Djordjevic, East Granby, CT (US); Sushil K. Kanwar, West Hartford, CT (US)

(73) Assignee: PL Medical Company LLC, New Britain, CT (US)

( * ) Notice: Subject to any disclaimer, the term of this patent is extended or adjusted under 35 U.S.C. 154(b) by 426 days.

(21) Appl. No.: 12/080,374

(22) Filed: Apr. 2, 2008

(65) Prior Publication Data

US 2008/0249550 A1    Oct. 9, 2008

Related U.S. Application Data

(60) Provisional application No. 60/921,738, filed on Apr. 4, 2007.

(51) Int. Cl.
*A61B 17/32* (2006.01)
(52) U.S. Cl. .......................................... 30/162; 606/167
(58) Field of Classification Search .................... 30/162, 30/163, 335, 320, 151; 606/167, 170, 172
See application file for complete search history.

(56) References Cited

U.S. PATENT DOCUMENTS

| 5,330,493 | A | * | 7/1994 | Haining | 606/167 |
| 5,571,127 | A | * | 11/1996 | DeCampli | 606/167 |
| 5,599,351 | A | * | 2/1997 | Haber et al. | 606/167 |
| 6,022,364 | A | * | 2/2000 | Flumene et al. | 606/166 |
| 7,527,635 | B2 | * | 5/2009 | Saito et al. | 606/167 |
| 2005/0021064 | A1 | * | 1/2005 | Lee | 606/167 |
| 2006/0212057 | A1 | * | 9/2006 | Djordjevic et al. | 606/167 |

* cited by examiner

*Primary Examiner* — Stephen Choi
(74) *Attorney, Agent, or Firm* — Alix, Yale & Ristas, LLP (57) ABSTRACT

A disposable safety scalpel comprises a handle and a blade carrier, which fit together such that the blade carrier can shift between a retracted position whereby a front portion of the handle covers or otherwise blocks contact with the sharp edge of the blade, and an extended position whereby the sharp edge of the blade protrudes beyond the handle. The handle has a substantially flat base portion that can be held by the forefinger of the surgeon for shifting of the carrier with the thumb between retracted and extended positions. When the carrier and blade are extended, the surgeon can hold only the base of the handle between the thumb and forefinger for cutting during surgery. The shifting between the retracted and deployed positions with only the fingers of one hand can be readily accomplished even in the presence of slippery fluids during surgery.

13 Claims, 8 Drawing Sheets

MINIATURE DISPOSABLE SAFETY SCALPEL

RELATED APPLICATION

This application claims priority under 35 U.S.C. 119(e) from U.S. Provisional Application No. 60/921,738 filed Apr. 4, 2007, for "Miniature Disposable Safety Scalpel", the entire disclosure of which is hereby incorporated by reference.

BACKGROUND

The present invention relates to surgical scalpels and especially to miniature scalpels.

In order to minimize any danger of accidental injury all currently produced surgical scalpels feature means to cover or otherwise protect the sharp edge of the blade whenever the scalpel is not deployed for use, including prior to disposal after the use. Ideally this protective means should be permanently attached to the scalpel and preferably be engaged and disengaged by fingers of one hand only.

SUMMARY

The disposable safety scalpel according to the present disclosure comprises a handle and a blade carrier, which fit together such that the blade carrier can shift between a retracted position whereby a front portion of the handle covers or otherwise blocks contact with the sharp edge of the blade, and an extended position whereby the sharp edge of the blade protrudes beyond the handle. The handle has a substantially flat base portion that can be held by the forefinger of the surgeon for shifting of the carrier with the thumb between retracted and extended positions. When the carrier and blade are extended, the surgeon can hold only the base of the handle between the thumb and forefinger for cutting during surgery.

The shifting between the retracted and deployed positions with only the fingers of one hand can be readily accomplished even in the presence of slippery fluids during surgery. Also, the sandwiching of handle, blade, and blade carrier according to the invention, results in an exceptionally thin scalpel. As a consequence, when the scalpel is deployed, the base of the handle where grasped, the overlapping region of the locking interaction and blade attachment, and the extended blade, present an overall slim appearance as viewed by the surgeon from above.

In an exemplary aspect, the scalpel comprises an elongated handle having a front and a back, outer and inner sides, and vertically opposite upper and lower edges. An elongated blade carrier has front and back ends, inner and outer sides, and vertically opposite upper and lower edges. The back of the handle has a base portion, the back of the carrier has a base portion, and each of the handle and carrier has a frontal protrusion that preferably narrows vertically toward the respective front ends, thereby defining respective vertical profiles. A blade is secured to the inner side of the carrier and projects from the front of the carrier laterally adjacent to the protrusion on the handle. The blade cutting edge faces away from the bottom edge of the carrier. Longitudinal guide tracks on one of the handle or carrier engage the other of the handle or carrier, whereby the tracks maintain the carrier and handle in close parallel axial alignment while the carrier and secured blade are shiftable longitudinally relative to the handle. A locking device is located at the back end of the carrier and includes a locking member at the inside of the carrier. Two locking elements are longitudinally spaced apart on the inside of the handle and aligned with the locking member on the carrier. In this manner, the locking member is selectively engageable with each locking element as the carrier and blade shift longitudinally between a rearward locked safety position in which the cutting edge of the blade is entirely within the profile of the frontal protrusion of the handle and a forward locked deployment position in which the cutting edge of the blade projects from the front end of the handle.

Preferably, the engageable parts of carrier and handle are of generally similar shape but have a different size, whereby the smaller member can slide in track guides of the larger member. As a further preference, the locking device in the base portion of the carrier has a longitudinally oriented lever arm with a tooth portion that is biased toward the handle so it can snap into either of two longitudinally spaced locking windows on the base portion of the handle as the blade carrier slides forward or backward in tracks of the handle. An actuating button or the like is on the opposite end of the lever arm, facing away from the handle, such that depressing the button lifts the toothed end out of one locking window so the carrier can be shifted and secured by engagement of the tooth in the other locking window.

The blade carrier and handle are well suited for cooperation as a miniature scalpel, but can be configured with a handle that is much longer than the carrier. Especially with the longer handle, the guide tracks can be on either the handle or the carrier.

BRIEF DESCRIPTION OF THE DRAWING

Embodiments of the invention will be described in greater detail below with reference to the accompanying drawing, in which.

DESCRIPTION

Figure 1:
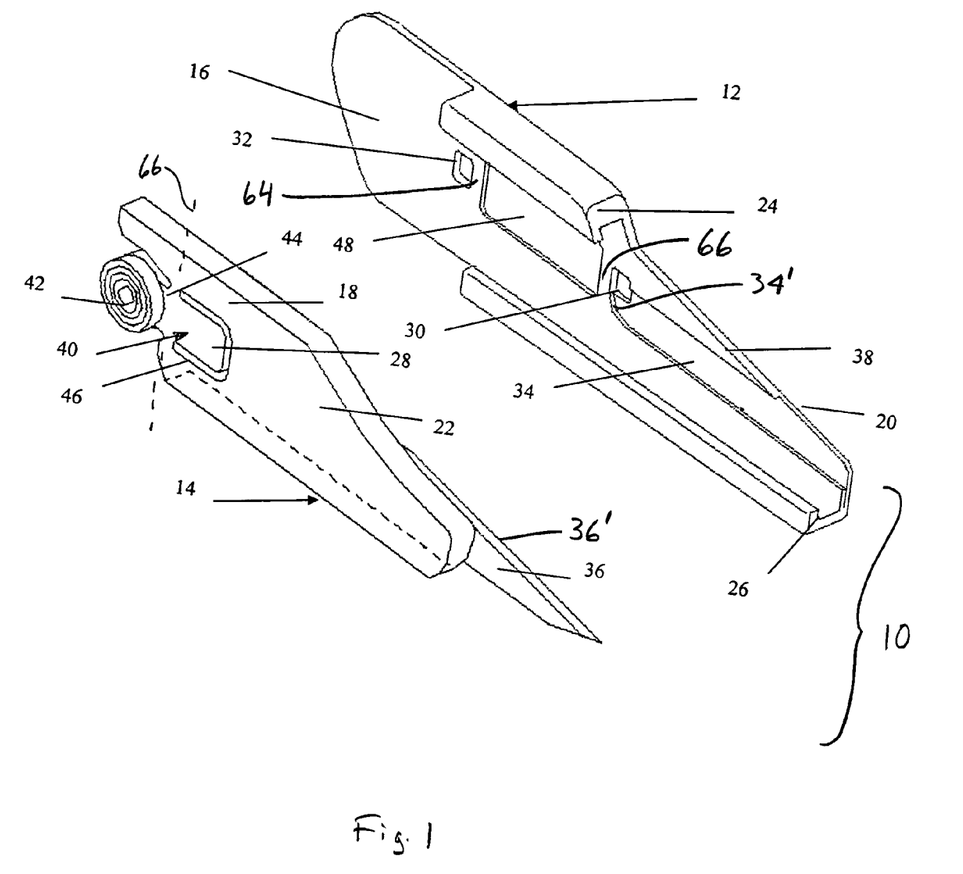
FIG. 1, is a perspective view of the blade carrier and the handle, prior to joining together to form a miniature safety scalpel according to aspects of the invention.

With reference first to FIG. 1, the miniature scalpel 10 comprises two main components: a compact handle and protection shield combination 12 and a blade carrier and blade assembly 14. For convenient and consistent reference, the sides of the handle and carrier that face each other will herein be deemed the "inside", whereas the respective opposite sides will be deemed the "outside".

The figure shows both main components prior to final assembly. Each part has a base portion 16, 18 in the back and a vertically narrowing protrusion 20, 22 at the front. In this embodiment the height of the base portion of the carrier 14 is less than the height of the base portion of the handle 12, and likewise the height of the protruding portion 22 of the carrier is correspondingly less than the height of the narrowing portion 20 of the handle. Because the overall shapes are similar but the carrier is smaller than the handle, the parts are subsequently assembled by inserting of the blade carrier in between the upper and lower guide tracks 24, 26 at the upper and lower edges of the handle and moving the blade carrier from right to left until the toggle lever tooth 28 on the locking device 40 passes the forward (first) locking element on the handle such as rectangular opening or window 30 and then engages with the rear (second) rectangular opening 32 of the handle. This is preferably confirmed by an audible clicking sound. The blade assembly is then ready for sterilization and packaging.

With further reference to FIGS. 2-9, a shallow groove or recess 34 is provided in the inside surface of the handle protrusion 20 for accommodating the rivet heads 58, 60 which attach the blade to the carrier body, and thereby minimize the lateral distance between the cutting edge 36' of blade 36 and the blade guide 38 of the handle when the blade is retracted. The left end 34' of this groove 34 at the same time prevents any over travel toward the left, which could cause possible disengagement. Similar means, such as a small interfering notch (not shown) in the lower guide track 26, prevents possible over travel beyond blade exposed position.

The handle 14 is substantially flat except that the upper guide track 24 projects transversely inward from the upper edge of the base portion 16 of the handle, and the lower track 26 projects transversely inward from the lower edge of the handle, keeping a uniform distance between them substantially equal to the uniform height of the base portion 18 of the carrier. The lower track 26 can extend from the forward portion of the base 16 substantially the full length of the front portion 20 of the handle, to cradle the lower edge of the front portion 22 of the carrier. The upper track preferably extends only along the forward portion of base 16, approximately spanning the openings 30, 32. The upper edge of the front portion 22 of the carrier is not contacted by the (foreshortened) upper track 24.

Figure 9:
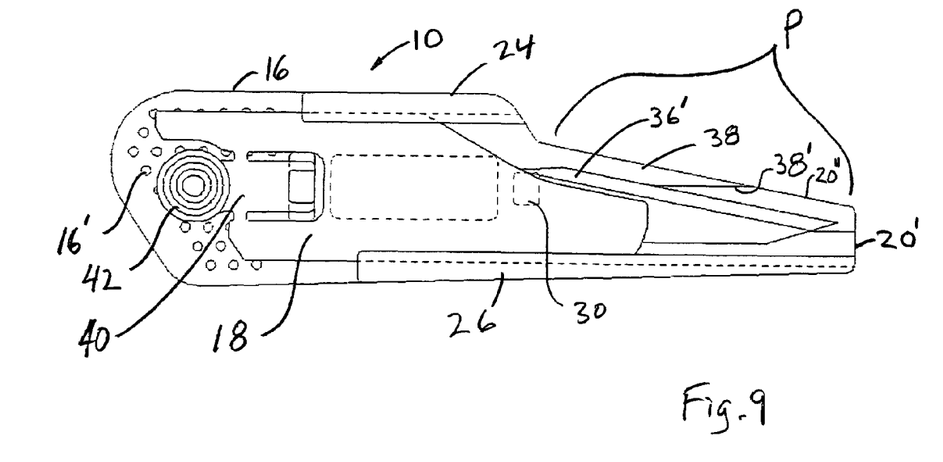
FIG. 9 is a side view of the scalpel with the blade retracted for protection.

In one embodiment as shown in detail in FIG. 9, the front portion of the handle has an inwardly projecting guide 38 for laterally contacting the cutting edge 36' of the retracted blade, which faces away from the bottom edge of the carrier. The upper and lower edges of the front portion of the handle define a vertical profile P, and the blade 36 remains within the profile when in the retracted position. The top edge of the guide 38 will thus block vertical contact with the edge 36' of the blade. The edge of the blade is angled obliquely as affixed to the carrier, and the guide upper edge has substantially the same profile angle. The front end 38' of the guide 38 does not reach the front tip 20' of the handle, but the top edge 20" of the handle rises above the cutting edge and likewise blocks vertical contact with the blade edge. The main purpose of the inward projection 38 of the guide in this embodiment is to provide lateral support to the blade edge 36 and thus maintain the blade edge in proper axial alignment during shifting.

In another embodiment the inwardly projecting structure at the location of the guide 38 could instead be formed as a hood, cover, spaced apart studs or other transverse projection, extending along the rear portion of the handle protrusion 20, to overly the cutting edge 36' of the blade and directly shield at least the rearward portion of the cutting edge when in the retracted position. For example, track 24 could be extended along profile P. As used herein, the term "shield" should be understood as encompassing structure that contacts or covers the cutting edge of the blade in a manner that blocks vertical access to the cutting edge.

Figure 8:
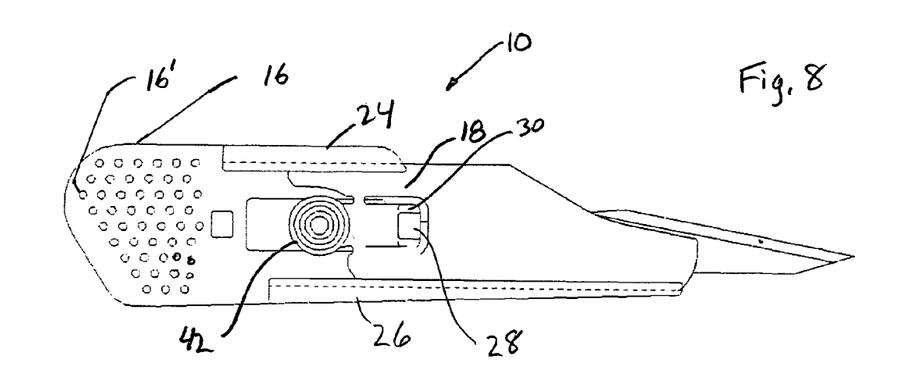
FIG. 8 is a side view of the scalpel with the blade exposed for use.

With particular reference to FIGS. 1, 8 and 9, the base portion 18 of the carrier has a longitudinally oriented locking device preferably in the form of a lever 40 that pivots about an axis passing through the carrier base. A locking arm cantilevered forward of the pivot axis includes a tooth portion 28 that is biased toward the handle 12 so it can snap into either of the two longitudinally spaced locking windows 30, 32 on the base portion of the handle as the blade carrier slides forward or backward in tracks 24, 26 of the handle. It is not necessary that the windows 30, 32 penetrate the full thickness of the handle. The biasing of the tooth 28 need not be via a separate member, but is preferably a result of the thickness of the lever 40 or tooth portion 28 relative to the separation distance between the base portions 16, 18 of the assembled device. An actuating arm is cantilevered toward the rear and has an actuating pad or button 42 such that depressing the button lifts the toothed end 28 out of one locking window so the carrier and blade can be shifted and secured by engagement of the tooth in the other locking window. The fulcrum of the lever is preferably formed by lateral integral web regions 44 that are thin or flexible enough to permit pivoting around the web centerlines (pivot axis) 67 that extend transverse to the lever 40. The button extends in free space behind the web 44, whereas the arm portion forward of the web is situated in a cut out 46 through the base 18.

Figure 7:
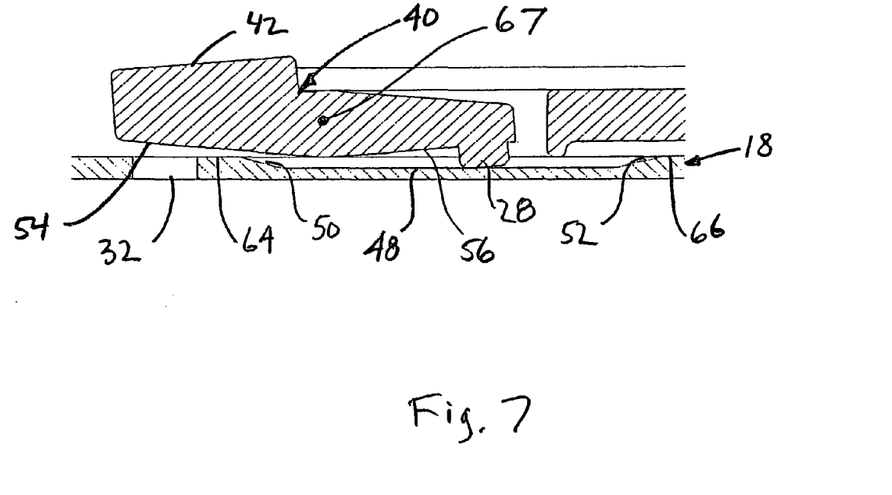
FIG. 7 shows the preferred profile of the region on which the tooth slides between the front and back locking windows.

Preferably, as best shown in FIGS. 1, 7, and 9, the back locking element 32 is located immediately forward of the textured surfaces 16' of the base of the handle, and the front locking element 30 is longitudinally spaced forward of the back locking element. The recess 48 in the handle extends from one web 64 adjacent the locking element 32 to another web 66 adjacent the other locking element 30 whereby during shifting of the carrier relative to the handle the locking member 28 rides in the recess 48 and upon further shifting from the recess into a locking element is deflected by and rides over a web. Preferably, each of the webs has a transition slope 50, 52 that rises from the recess to a flat surface immediately adjacent to the respective locking element. To facilitate pivoting of the locking device, the actuator arm and locking arm have obliquely angled inner surfaces 54, 56 facing the handle. The pivot axis is shown at 67.

Figure 5A:
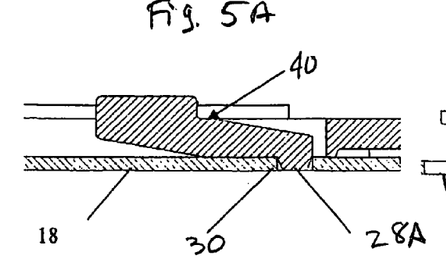
FIGS. 5A and 5B show the operation of a first version of the locking arm.
Figure 5B:
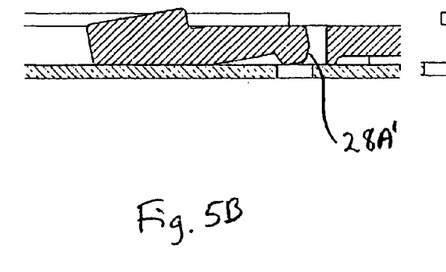
Figure 6A:
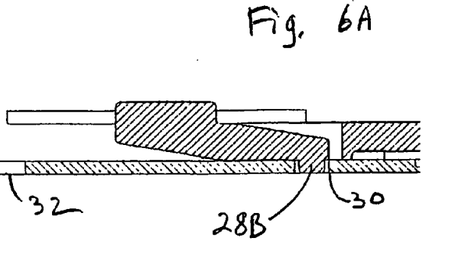
FIGS. 6A and 6B show the operation of another version of the locking arm.
Figure 6B:
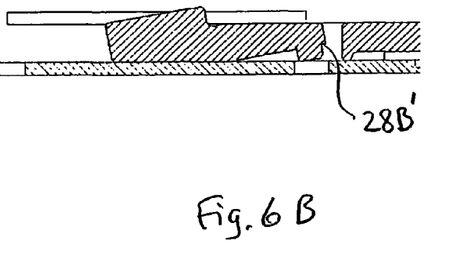

FIGS. 5A and 5B show two options 28A and 28B for the tooth. The tooth 28A has a tapered or frustoconical shape 28A', whereas tooth 28B' is substantially rectangular or cylindrical with an annular shoulder 28B'.

Figure 2:
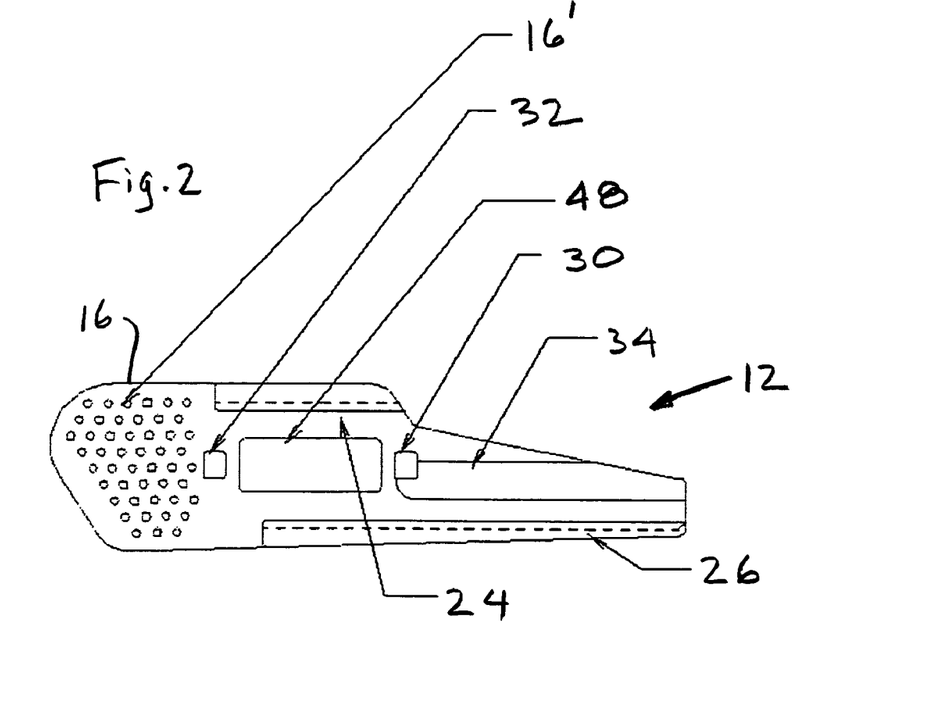
FIGS. 2 and 3 are each elevation views of blade carriers showing different versions of anti-slippage surfaces on the handle portions.
Figure 3:
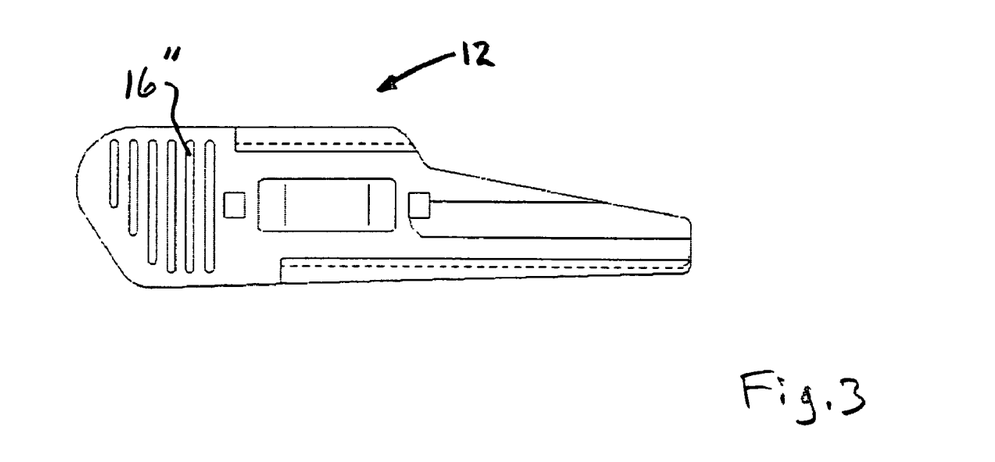
Figure 4A:
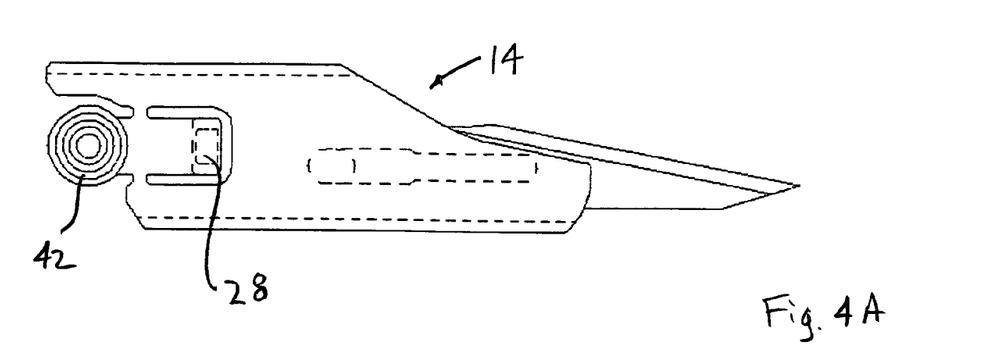
FIGS. 4A and 4B show the outside and the inside of the blade carrier, respectively.
Figure 4B:
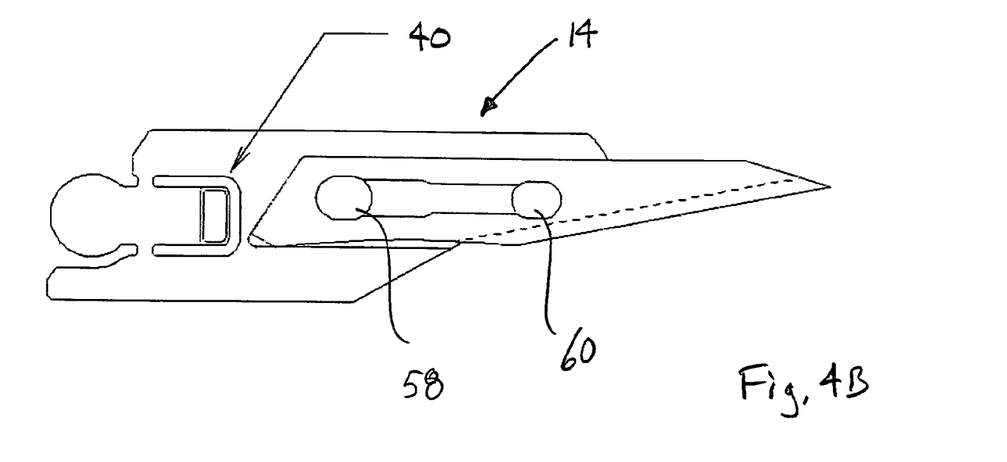

As shown in FIGS. 2 and 3, the textured anti-slippage surfaces on both side surfaces of the base portion of the handle can be dimples 16', shallow depressions, vertical channels 16" or perforations. Also, a deeply channeled or swirled surface on the actuating button 42 can be provided. This minimizes the accumulation of blood-induced finger slippage where the surgeon is expected to exert relatively opposite, axially directed forces with the forefinger and thumb to extend or retract the blade, or transverse force to lift the tooth 28 out of a locking window, or uniformly axially directed forces to produce a cutting action during surgery.

The above described design is very compact. In the extended position the device is the size of a conventional fixed blade thumb scalpel. Both the handle and carrier components can be manufactured in plastic with by very simple dies. Because the blade is visible even in the retracted position, neither of the parts needs to be transparent. The material of both components can be identical (type and color) making recycling much easier.

As shown in FIGS. 2, 3, 8 and 9, the base portion 18 of the carrier including the locking device 40 overlays the base portion 16 of the handle when the scalpel is in the locked safety position. Preferably one locking element 32 is located immediately forward of the textured surfaces of the base of the handle, and the other locking element 30 is longitudinally spaced forward of the one locking element 32. Furthermore, in the locked safety position of the scalpel the carrier and blade lie within the front, back, and upper and lower edges of the handle, i.e. within the perimeter or profile P of the handle. This is a consequence of the overall similar but smaller shape of the carrier. In the deployed position of the scalpel the base 18 of the carrier is forward of the base 16 of the handle, whereby the outer and inner surfaces of the base 16 of the handle can be grasped between the thumb and forefinger for manipulating the blade, while the blade projects forwardly from the handle.

Also evident in FIG. 8, is that in the deployed position, the locking engagement of the tooth 28 in the window 30 is situated nearly vertically between portions of both upper and lower tracks 24, 26 that engage upper and lower edges of the carrier. This provides high stability to the lock.

In FIG. 9, the cutting edge of the blade partially overlaps laterally with the shield and the cutting edge is entirely below the upper edge of the handle protrusion, but the angle of the blade is such that when the carrier is deployed as per FIG. 8, a portion of the of the cutting edge overlaps but is above the protrusion of the handle while the remainder of the cutting edge is forward of the protrusion.

Figure 10:
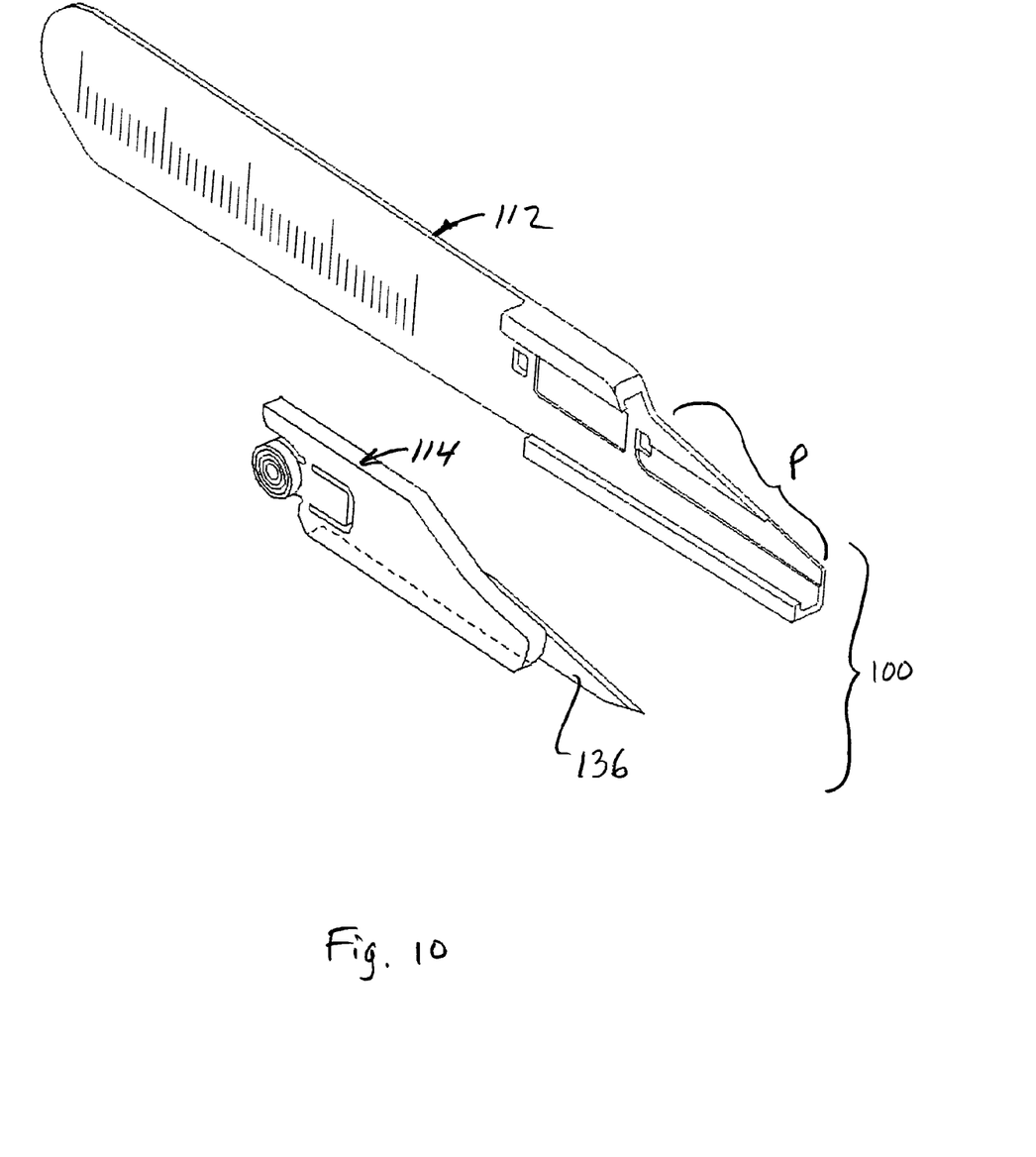
FIG. 10 is a view similar to FIG. 1, but for a second embodiment modified for use with a full length handle.

As shown in FIG. 10, a very similar blade carrier can be used for full length and, partially disposable scalpels. In the full length embodiment 100, the handle 112 extends well back of the carrier 114, i.e., at least three times the length. One of ordinary skill can optimize the profile P' of the handle to accommodate and protect a variety of blades 136. This affords the possibility of providing a uniform handle that can accommodate a variety of blade sizes or types. Such variety can in most instances rely on a uniform carrier; however, the protrusion at the front end of the handle must be sized to provide full protection for the variety of blades.

Figure 11:
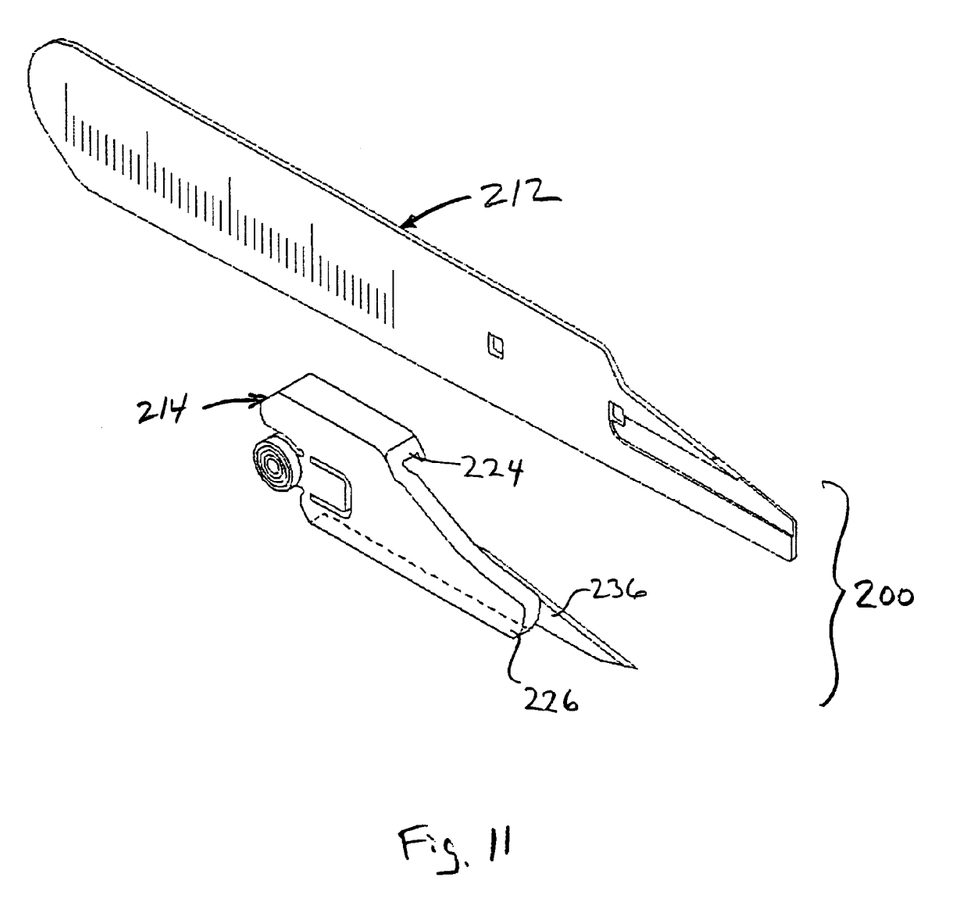
FIG. 11 is a variation of the scalpel of FIG. 10, wherein the sliding track is on the carrier rather than on the handle.

Especially in but not limited to the embodiment of a universal handle and blade carrier, relocation of the guide track 224, 226 from the handle 212 to the blade carrier 214 can simplify the shape of the handle to become a flat piece of material. One such embodiment is shown in FIG. 11. Because of the simplicity, this version would be ideally suitable for application with a semi disposable scalpel (scalpel with reusable stainless steel handle 212). Additional means (not shown) could be provided to protect and cover the blade 236 while still stored in its sterile pouch (prior to being attached to the handle 212). This protection could for example be provided by a breakaway extension of the blade carrier 214 temporarily covering the blade 236 or by a loose flat plastic flap inserted between both guide tracks 224, 226 covering the blade until it is pushed out by the handle during the process of attaching the blade carrier to the handle.

Figure 12:
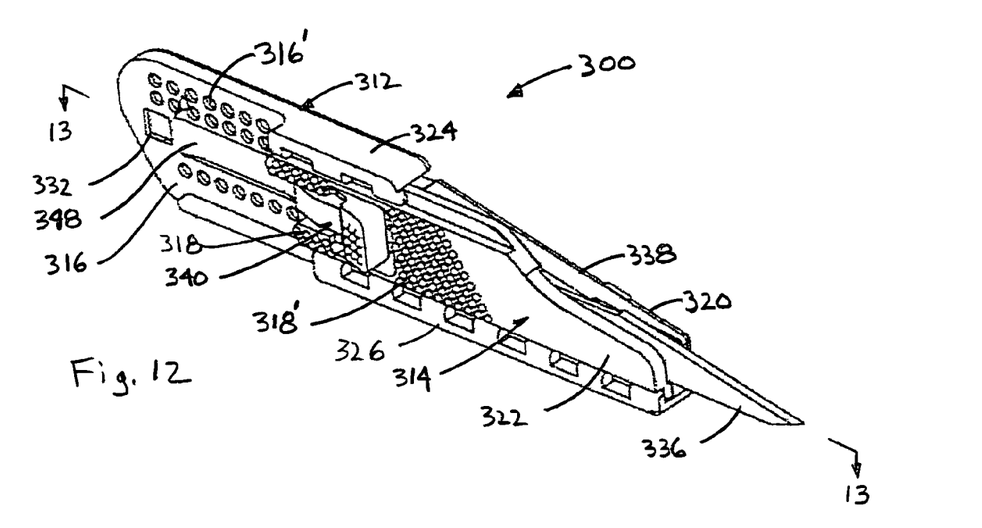
FIG. 12 is a perspective view of another embodiment of the miniature scalpel.
Figure 13:
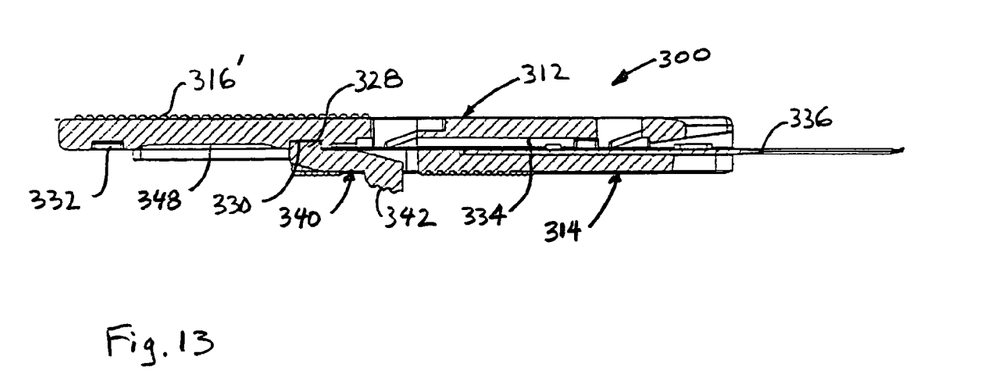
FIG. 13 is a section view along line 13-13 of FIG. 12.

Another embodiment of the miniature scalpel 300 is shown in FIGS. 12 and 13, which embodiment can also be adapted with the variations shown in FIGS. 10 and 11. In this embodiment the orientation of the locking device on the carrier is longitudinal reversed and the locking elements on the handle are commensurately longitudinally set farther back into the base of the handle, while maintaining the slim lines and improving the ease of use. The last two digits in the numeric identifiers in FIGS. 12 and 13 refer to functionally similar structure identified with the same two digits in FIGS. 1-9.

The scalpel 300, shown in the deployed condition, has a handle 312 and a blade carrier 314 with respective base portions 316, 318 in the back and a vertically narrowing protrusion 320, 322 at the front. The parts are assembled by inserting of the blade carrier in between the upper and lower guide tracks 324, 326 at the upper and lower edges of the handle and moving the blade carrier from right to left until the toggle lever tooth 328 on the locking device 340 passes the forward (first) locking element on the handle such as rectangular opening or window 330 and then engages with the rear (second) rectangular opening 332 of the handle.

A shallow groove or recess 334 is provided in the inside surface of the handle protrusion 320 for accommodating the rivet heads which attach the blade 336 to the carrier body, and thereby minimize the lateral distance between the cutting edge of blade 336 and the blade guide 338 of the handle when the blade is retracted.

The base portion 318 of the carrier including the locking device 340 overlays the base portion 316 of the handle when the scalpel is in the locked safety position. One locking element 332 is located close at the back end of the handle and the other locking element 330 is spaced longitudinally forward. Preferably, as shown in FIG. 13, both locking elements 330, 332 on the inside of the back 316 of the handle are within the longitudinal span of the textures surface 316' on the outside of the base of the handle. The recess 348 in the handle extends from one web adjacent the locking element 332 to another web adjacent the other locking element 330 whereby during shifting of the carrier relative to the handle the locking member 328 rides in the recess 348 and upon further shifting from the recess into a locking element is deflected by and rides over a web.

The locking device 340 has the tooth 328 toward the back and the actuating pad 342 toward the front of the base 318. The locking device 340 can be a simple lever as in the previously described embodiments, or the actuating and locking arms can be laterally supported for a pivoting type movement, by a pair of legs or the like, such as described in U.S. Pat. No. 7,153,317. The outside back of the carrier has a no-slip, textured surface 318' surrounding and forward of the locking device 340. This provides a greater textured contact area for the thumb during shifting, than the embodiment of FIGS. 1-9.

As in the other embodiments described herein, the front portion of the handle has an inwardly projecting guide 338 for laterally contacting the cutting edge of the retracted blade 336. The upper and lower edges of the front portion of the handle define a vertical profile and the blade 336 remains within the profile when in the retracted position. The top edge of the guide 338 will thus block vertical contact with the edge 336 of the blade.

For many users, the scalpel 300 according to FIGS. 12 and 13 should feel better balanced and stable. With the actuating button 342 located more forwardly, closer to the center of the device, the tendency of any incidentally applied torque to rotate the carrier is reduced.

The invention claimed is:
1. A surgical scalpel comprising:
   a handle elongated on a handle axis and having a front, a back, outer and inner sides, and upper and lower edges;
   a blade shield at the upper edge of the handle, projecting inwardly;
   a blade carrier elongated on a carrier axis, having a front, a back, inner and outer sides, and upper and lower edges;
   a blade secured to the inner side of the carrier and projecting from the front of the carrier, the blade having a cutting edge that faces away from the lower edge of the carrier, toward the blade shield;

upper and lower longitudinal guide tracks along upper and lower edges of one of the handle or carrier engaging upper and lower edges respectively on the other of the handle or carrier, whereby the tracks maintain the carrier and handle in parallel axial alignment while the carrier and secured blade are shiftable longitudinally relative to the handle;

a locking device at the back of the carrier including an actuator at the outside of the carrier and a locking member at the inside of the carrier;

two locking elements longitudinally spaced apart on the inside of the handle and aligned with the locking member on the carrier;

whereby the locking member is selectively engageable with each locking element as the carrier and blade shift longitudinally between a rearward locked safety position in which the cutting edge of the blade is protected by said shield and a forward locked deployment position in which the cutting edge of the blade projects in front of said shield and the front of the handle;

wherein the back of the handle has a base portion with textured outer and inner surfaces;

the back of the carrier has a base portion including said locking device which overlays the base portion of the handle when the scalpel is in the locked safety position;

in the locked safety position of the scalpel the carrier and blade lie within the front, back, and upper and lower edges of the handle;

in the deployed position of the scalpel the base of the carrier is forward of the base of the handle, whereby the outer and inner surfaces of the base portion of the handle can be grasped between the thumb and forefinger for manipulating the blade;

the locking device comprises a lever, including an actuator arm having an outwardly projecting pad forming said actuator, and a locking arm having said locking member projecting inwardly;

one of said locking elements is located immediately forward of the textured surfaces of the base of the handle;

another of said locking elements is longitudinally spaced forward of said one locking element;

a recess in the handle is situated between the locking elements and is separated from the locking elements by one intervening web adjacent the one locking element and another intervening web adjacent the other locking element;

whereby during said shifting of the carrier relative to the handle the locking member rides in said recess and upon further shifting from the recess into a locking element is deflected by and rides over a web.

2. The scalpel of claim 1, wherein each of the handle and carrier has a protrusion that narrows away from the respective base portion toward respective front ends of the handle and carrier;

the height of the base portion of the carrier is less than the height of the base portion of the handle;

the height of the protruding portion of the carrier is correspondingly less than the height of the protruding portion of the handle; and the upper and lower edges of the blade carrier are in upper and lower guide tracks of the handle.

3. The scalpel of claim 2, wherein the upper guide track extends along only a portion of the upper edge of the base portion of the handle;

the lower guide track extends from the base portion to the front end of the handle; and the blade shield extends along the upper edge of the protruding portion of the handle, forward of the upper track.

4. The scalpel of claim 1, wherein the actuator arm and the locking arm have inner surfaces facing the handle; and the inner surface of the actuator arm is obliquely angled relative to the inner surface of the locking arm.

5. The scalpel of claim 1, wherein the locking elements are openings in said handle and the locking member is a tooth sized to engage said openings.

6. The scalpel of claim 1, wherein the locking arm is biased toward the handle.

7. The scalpel of claim 1, wherein the blade is secured to the carrier by a plurality of longitudinally spaced apart rivets; and the handle has a longitudinal recess in which the rivets ride during the shifting of the carrier relative to the handle.

8. The scalpel of claim 1, wherein the upper and lower longitudinal guide tracks are located along the upper and lower edges of the carrier engaging upper and lower edges of the handle, whereby the tracks maintain the carrier and handle in parallel axial alignment while the carrier and secured blade are shiftable longitudinally relative to the handle.

9. The scalpel of claim 8, wherein the locking elements are openings in said handle and the locking member is a tooth sized to engage said openings;

the locking member is biased toward the handle;

the blade is secured to the carrier by a plurality of longitudinally spaced apart rivets;

the handle has a longitudinal recess in which the rivets ride during the shifting of the carrier relative to the handle; and the blade shield is situated adjacent to and extending longitudinally along a portion of the recess, facing the blade.

10. The scalpel of claim 8, wherein the handle is at least three times as long as the carrier and blade.

11. The scalpel of claim 1, wherein each of the handle and carrier has a protrusion that narrows toward respective front ends of the handle and carrier;

the locking elements are openings in said handle and the locking member is a pivoting tooth biased toward and sized to engage said openings;

the blade is secured to the carrier by a plurality of longitudinally spaced apart rivets;

the protruding portion of the handle has a longitudinal recess in which the rivets ride during the shifting of the carrier relative to the handle; and the blade shield projects inwardly adjacent to and extends longitudinally along the recess, facing the blade.

12. The scalpel of claim 1, wherein each of the handle and carrier has a protrusion that narrows toward respective front ends of the handle and carrier;

the protruding portion of the carrier has a height that is correspondingly less than the height of the protruding portion of the handle;

the blade shield projects inwardly along a rearward extend of the protruding portion of the handle and faces the blade; and in the safety lock position of the scalpel, the blade shield overlies a rearward portion of the blade cutting edge and the protruding portion of the handle forward of the shield provides protection for the forward portion of the blade cutting edge.

13. A surgical scalpel comprising:

a handle elongated on a handle axis and having a front, a back, outer and inner sides, and upper and lower edges;

a blade shield at the upper edge of the handle, projecting inwardly;

a blade carrier elongated on a carrier axis, having a front, a back, inner and outer sides, and upper and lower edges;

a blade secured to the inner side of the carrier and projecting from the front of the carrier, the blade having a cutting edge that faces away from the lower edge of the carrier, toward the blade shield;

upper and lower longitudinal guide tracks along upper and lower edges of one of the handle or carrier engaging upper and lower edges respectively on the other of the handle or carrier, whereby the tracks maintain the carrier and handle in parallel axial alignment while the carrier and secured blade are shiftable longitudinally relative to the handle;

a locking device at the back of the carrier including an actuator at the outside of the carrier and a locking member at the inside of the carrier;

two locking elements longitudinally spaced apart on the inside of the handle and aligned with the locking member on the carrier;

whereby the locking member is selectively engageable with each locking element as the carrier and blade shift longitudinally between a rearward locked safety position in which the cutting edge of the blade is protected by said shield and a forward locked deployment position in which the cutting edge of the blade projects in front of said shield and the front of the handle;

wherein the locking device comprises a lever, including an actuator arm extending toward the front of the carrier and having an outwardly projecting pad forming said actuator, and a locking arm extending toward the back of the carrier and having said locking member projecting inwardly;

both of said locking elements are in the base of the handle;

a recess in the base of the handle is separated from the locking elements by one intervening web adjacent the one locking element and another intervening web adjacent the other locking element, and extends from one web adjacent one locking element to another web adjacent the other locking element;

whereby during said shifting of the carrier relative to the handle the locking member rides in said recess and upon further shifting from the recess into a locking element is deflected by and rides over a web.

* * * * *